US010632042B2

(12) United States Patent
Schlosser

(10) Patent No.: US 10,632,042 B2
(45) Date of Patent: Apr. 28, 2020

(54) GUIDING MEANS FOR ADMINISTERING ACUPUNCTURE AND OTHER HEALING PROCEDURES

(71) Applicant: MS GOOD ENERGIES LIMITED, Nicosia (CY)

(72) Inventor: Michael Schlosser, Haifa (IL)

(73) Assignee: MS GOOD ENERGIES LIMITED, Nicosia (CY)

( * ) Notice: Subject to any disclaimer, the term of this patent is extended or adjusted under 35 U.S.C. 154(b) by 919 days.

(21) Appl. No.: 14/903,237

(22) PCT Filed: Jul. 1, 2014

(86) PCT No.: PCT/IL2014/050587
§ 371 (c)(1),
(2) Date: Jan. 6, 2016

(87) PCT Pub. No.: WO2015/004653
PCT Pub. Date: Jan. 15, 2015

(65) Prior Publication Data
US 2016/0136045 A1    May 19, 2016

(30) Foreign Application Priority Data
Jul. 8, 2013    (IL) .......................................... 227374

(51) Int. Cl.
*A61H 39/02* (2006.01)
*A61N 5/06* (2006.01)
(Continued)

(52) U.S. Cl.
CPC .............. *A61H 39/02* (2013.01); *A41B 11/00* (2013.01); *A41D 13/1236* (2013.01);
(Continued)

(58) Field of Classification Search
CPC .... A61H 39/00; A61H 39/002; A61H 39/007; A61H 39/02; A61H 39/04; A61H 39/08;
(Continued)

(56) References Cited

U.S. PATENT DOCUMENTS 5,405,310 A * 4/1995 Yoo ........................ A61H 39/04
601/134
5,663,828 A 9/1997 Knowles et al.
(Continued)

FOREIGN PATENT DOCUMENTS

CN    2077278 U    5/1991
CN    2254347 Y    5/1997
(Continued)

OTHER PUBLICATIONS

"International Application Serial No. PCT/EP2013/065223, International Search Report dated Sep. 30, 2014", 3 pgs.
(Continued)

*Primary Examiner* — Victoria J Hicks
*Assistant Examiner* — Rachel A Berezik
(74) *Attorney, Agent, or Firm* — Schwegman Lundberg & Woessner, P.A.

(57) ABSTRACT

The invention is guiding means that are adapted to serve as guides to accurately locate specific locations on the body to be stimulated in order to prevent, diagnose, and treat specific types of diseases and other conditions in humans and animals. The invention includes specially modified and personalized articles of clothing and an apparatus for supporting an organ of a human or animal body adapted for accurately positioning and orienting the organ with respect to each other a device for administering the stimulation or the healing process. The apparatus and embodiments of the articles of clothing are adapted as stands that support devices used to apply stimulation to the location. The applied
(Continued)

stimulation can be any of the therapies which depend on the application of energy or force to specific locations on the body.

4 Claims, 3 Drawing Sheets

(51) Int. Cl.

| | | |
|---|---|---|
| *A61H 39/08* | (2006.01) | |
| *A61H 39/04* | (2006.01) | |
| *A61H 39/00* | (2006.01) | |
| *A61H 7/00* | (2006.01) | |
| *A61H 11/00* | (2006.01) | |
| *A41B 11/00* | (2006.01) | |
| *A41D 13/12* | (2006.01) | |
| *A41D 19/00* | (2006.01) | |
| *A41F 9/00* | (2006.01) | |
| *A41F 1/00* | (2006.01) | |
| *A42B 3/04* | (2006.01) | |
| *A61F 5/37* | (2006.01) | |
| *A61N 5/067* | (2006.01) | |
| *A42B 1/00* | (2006.01) | |

(52) U.S. Cl.
CPC ......... *A41D 19/0013* (2013.01); *A41F 9/002* (2013.01); *A42B 1/006* (2013.01); *A42B 3/04* (2013.01); *A61F 5/37* (2013.01); *A61H 7/006* (2013.01); *A61H 11/00* (2013.01); *A61H 39/002* (2013.01); *A61H 39/04* (2013.01); *A61H 39/08* (2013.01); *A61N 5/0619* (2013.01); *A61H 2039/005* (2013.01); *A61H 2201/164* (2013.01); *A61H 2201/1604* (2013.01); *A61H 2201/165* (2013.01); *A61H 2201/1635* (2013.01); *A61H 2205/02* (2013.01); *A61H 2205/065* (2013.01); *A61H 2205/12* (2013.01); *A61N 2005/067* (2013.01); *A61N 2005/0643* (2013.01)

(58) Field of Classification Search
CPC .. A61H 39/086; A61H 2039/005; A61H 7/00; A61H 7/001; A61H 7/002; A61H 7/003; A61H 7/004; A61H 7/007; A61H 2007/009; A61H 11/00; A61H 11/02; A61H 1/005; A61H 1/001; A61H 1/003; A61H 1/0285; A61H 1/0288; A61H 2201/1657; A61H 2201/1676; A61H 2201/1666; A61H 2201/1673; A61H 2201/1683; A61H 2201/1685; A61H 2201/1635; A61H 2201/1638; A61H 2201/164; A61H 2201/1642; A61H 15/00; A61H 15/02; A61H 15/0092; A61H 15/0078; A61H 15/0085; A61H 2015/0057; A61H 7/006; A61H 2201/165; A61H 2201/1604; A61H 2205/02; A61H 2205/065; A61H 2205/12; A61N 5/0619; A61N 2005/0643; A61N 2005/067; A41D 19/0013; A41D 13/1236; A61F 5/37; A61F 5/01; A61F 5/0102; A41F 9/002; A61G 13/12; A61G 13/1235; A61G 13/124; A61G 13/1245; A61G 13/125; A61G 13/126; A61G 13/128; A61G 13/1285; A61G 13/129; A61G 13/1295; A42B 1/006; A42B 3/04; A41B 11/00
See application file for complete search history.

(56) References Cited

U.S. PATENT DOCUMENTS

| | | | |
|---|---|---|---|
| 6,306,160 B1 | 10/2001 | Nidetzky | |
| 6,665,554 B1 | 12/2003 | Charles et al. | |
| 7,179,278 B2 | 2/2007 | Schikora | |
| 2001/0014781 A1* | 8/2001 | Nissim | A61H 7/001 601/133 |
| 2001/0041851 A1* | 11/2001 | Peyton | A61H 39/04 601/133 |
| 2004/0044384 A1* | 3/2004 | Leber | A61N 5/0619 607/88 |
| 2004/0077937 A1 | 4/2004 | Yarden | |
| 2004/0158176 A1* | 8/2004 | Park | A61H 15/0078 601/18 |
| 2004/0243034 A1* | 12/2004 | Kim | A61N 5/0625 601/100 |
| 2007/0129713 A1 | 6/2007 | Weber | |
| 2008/0177212 A1* | 7/2008 | Kim | A61H 15/00 602/33 |
| 2010/0137762 A1* | 6/2010 | Tsai | A61H 7/002 601/134 |

FOREIGN PATENT DOCUMENTS

| | | |
|---|---|---|
| CN | 201481776 U | 5/2010 |
| CN | 101982161 A | 3/2011 |
| CN | 201861952 U | 6/2011 |
| CN | 102309405 A | 1/2012 |
| CN | 102716553 A | 10/2012 |
| CN | 202526546 U | 11/2012 |
| CN | 202664254 U | 1/2013 |
| CN | 202920613 U | 5/2013 |
| RU | 10566 U1 | 8/1999 |
| RU | 2258497 C2 | 8/2005 |
| RU | 2336069 C1 | 10/2008 |
| RU | 97269 U1 | 9/2010 |
| SU | 952252 A1 | 8/1982 |
| WO | WO-2006081883 A2 | 8/2006 |
| WO | WO-2015004653 A1 | 1/2015 |

OTHER PUBLICATIONS

"International Application Serial No. PCT/IL2014/050587, International Preliminary Report on Patentability dated Jan. 12, 2016", 8 pgs.
"International Application Serial No. PCT/L2014/050587, International Written Opinion dated Sep. 30, 2014", 5 pgs.
"Israeli Application Serial No. 2710955, Office Action dated Aug. 2, 2016", w/ English Translation, 4 pgs.
"Chinese Application No. 201480039134.2, Office Action dated Dec. 5, 2016", w/ English Translation, (Dec. 5, 2016), 10 pgs.
"European Application Serial No. 14 82 3875, Supplementary Partial European Search Report dated Feb. 10, 2017", (Feb. 10, 2017), 4 pgs.
"Russian Application Serial No. 2016103867/14 dated Sep. 8, 2018", (Sep. 28, 2018), 10 pgs.
"Indian Application Serial No. 201627001131, Examination Report dated Jan. 9, 2020", (dated Jan. 9, 2020), 6 pgs.

\* cited by examiner

GUIDING MEANS FOR ADMINISTERING ACUPUNCTURE AND OTHER HEALING PROCEDURES

PRIORITY APPLICATIONS

This application is a U.S. National Stage Filing under 35 U.S.C. § 371 from International Application No. PCT/IL2014/050587, filed on 1 Jul. 2014, and published as WO 2015/004653 on 15 Jan. 2015, which claims the benefit under 35 U.S.C. § 119 to Israeli Application No. 227374, filed on 8 Jul. 2013; each of which is incorporated herein by reference in its entirety.

FIELD OF THE INVENTION

The invention is from the field of medical devices. Specifically the invention is from the field of medical devices that assist in supporting devices used for administering acupuncture, bio-stimulation, and other therapies and healing procedures at the specific locations on a human or animal body at which these therapies should be applied.

BACKGROUND OF THE INVENTION

Acupuncture is one or of the oldest methods of treating disease having been used by the Chinese for over 4000 years. Without going into the philosophy behind it, the traditional Chinese method (TCM) is based on stimulating specific points on the body known as acupuncture points by penetrating the skin with thin sharp needles and manipulating the needles. The acupuncture points are located on paths called meridians through which energy flows throughout the body. Also a long standing aspect of TCM is a therapy called moxibustion, which involves burning a herb at an acupuncture point or in association with a needle.

Over the millennia that have passed since the origins of the practice of acupuncture new systems have evolved that use acupuncture points and meridians not recognized in the traditional Chinese method (TCM). Additionally new methods of applying the therapy that are non-invasive and do not require the use of needles have been devised. These methods include, for example, electric acupuncture, acupressure, and laser acupuncture.

Lasers are used in acupuncture in two ways: firstly, low-intensity non-thermal laser irradiation is used to stimulate traditional acupuncture points instead of needles; and secondly, longer wavelength infrared radiation is used to simulate the traditional acupuncture technique of moxibustion. Many different apparatuses have been described in the patent and non-patent literature for use in laser acupuncture. Some examples are:

U.S. Pat. No. 6,306,160 describes a hand held device that comprises an electrode used to locate acupuncture points by measuring skin resistance and a 3 mw diode laser that emits light with a wavelength of 635-670 nm to stimulate the acupoint.

U.S. Pat. No. 7,179,278 describes an apparatus in which one or more remote laser sources that emit light at 350-980 nm are optically linked by fiber optics to a handpiece that is in contact with the skin of the patient. The handpiece comprises two electrodes to measure skin resistance. The penetration depth is adjusted by changing the wavelength and also by reducing the diameter of the optical fiber as it approaches the tip of the handpiece.

US 2007/0129713 describes a laser needle for performing combined laser therapy and electric therapy. The output beam from a remote diode laser is conducted to the patient by an optical fiber. At its distal end the optical fiber is surrounded by a metal jacket having a disk attached to its lower end. The disk serves to distribute the electric current of the electric acupuncture over a larger area and also to aid in attaching the laser needle to the body of the patient.

CN102716553 is an example of a publication that describes an apparatus comprising two lasers that provides the combined effects of needle and moxibustion. The first laser is a red laser (635 nm) to simulate the effect of the needles and the second laser produces an output wavelength in the range of 1250-10000 nm to simulate the effect of thermal moxibustion.

CN101982161A and CN102309405A describe shirts on the outer surface of which have been marked acupuncture channels and points. CN202526546U describes articles of clothing adapted for acupuncture or moxibustion therapy by providing holes through the material at the location of acupoints. CN2254347Y and CN202664254U describe acupuncture massage clothes that respectively have plastic needles and silica gel or soft plastic massage mats on the inside of the clothing located at acupoints.

It is a purpose of the present invention to provide equipment that assists trained persons to carry out acupuncture, bio-stimulation, and other therapies and healing procedures in a clinical environment and allows untrained persons to carry out the procedure on himself, herself, or on another person in their homes.

It is another purpose of the present invention to provide personalized items of clothing to be used to assist in carrying out acupuncture, bio-stimulation, and other therapies and healing procedures by means of holes that are made in the item of clothing according to the anatomy of the specific patient at the location at which the treatment should be applied that is relevant to her/his condition.

It is another purpose of the present invention to provide an apparatus that functions as a stand to support a device at the correction locations and orientation for stimulating and/or healing the location at which the treatment should be applied that is relevant for treatment of a specific condition.

Further purposes and advantages of this invention will appear as the description proceeds.

SUMMARY OF THE INVENTION

In a first aspect the invention is an apparatus adapted to support and to accurately position and orient an organ of a human or an animal body and a device adapted for administering acupuncture, bio-stimulation, and other therapies and healing procedures with respect to each other at a specific location on a human or animal body in order to prevent, diagnose, and treat specific types of diseases and other conditions in humans and animals.

An embodiment of the apparatus of the invention comprises:
 a. a base plate;
 b. a rigid bridge rigidly attached to the base plate;
 c. a platform located between the base plate and the bridge. The platform is mounted to the base plate in such a way that it has two linear degrees of freedom that allow linear motion in directions parallel to two perpendicular sides of the base plate and one rotational degree of freedom around an axis perpendicular to the base plate that passes through the center of the platform;

d. at least one window or opening in the top of the bridge that allows observation of the treatment area on the platform;

e. at least one opening in the center of the bridge through which a device adapted for administering acupuncture, bio-stimulation, and other therapies and healing procedures can stimulate a specific location on an organ of a human or animal body that is present on the platform; and f. at least one hinge connected to a framework that supports a device adapted for administering acupuncture, bio-stimulation, and other therapies and healing procedures to the bridge, such that the device adapted for administering acupuncture, bio-stimulation, and other therapies and healing procedures can be tilted relative to the surface of the bridge.

In embodiments of the apparatus of the invention the device that is adapted for administering acupuncture, bio-stimulation, and other therapies and healing procedures is one of: traditional acupuncture needles, acupuncture needles supplied as auto-injectors, a laser beam, a device for applying non-coherent light, a device for applying pressure, a device for applying heat, and a device for applying electricity or a combination of the above mentioned methods.

Embodiments of the apparatus of the invention comprise locking mechanisms for the translational, rotational, and tilt motions. The locking mechanisms may comprise a series of marks that identifies the position at which each of the respective locking mechanisms is locked.

In a second aspect the invention is an article of clothing that is specially modified and personalized by making holes in the article of clothing at the exact location that corresponds to specific locations on the surface of the body of a human or animal specific that are effective for administering acupuncture, bio-stimulation, and other therapies and healing procedures for the purpose of diagnosing, preventing, and treating specific types of diseases or other conditions.

In embodiments of the article of clothing of the invention the material of which at least a part of the article of clothing is made is transparent.

Embodiments of the article of clothing of the invention comprise ridges around the holes or a framework attached to the article of clothing over the holes, wherein the ridges or the framework are adapted to help to hold a device adapted for administering acupuncture, bio-stimulation, and other therapies and healing procedures in a fixed position and orientation over the holes.

In embodiments of the article of clothing of the invention the device adapted for administering acupuncture, bio-stimulation, and other therapies and healing procedures is one of: traditional acupuncture needles, acupuncture needles supplied as auto-injectors, a laser beam, a device for applying non-coherent light, a device for applying pressure, a device for applying heat, and a device for applying electricity or a combination of them.

In embodiments of the article of clothing of the invention the article is one of: a glove, a sock, a helmet, a cap, and a belt.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Figure 1:
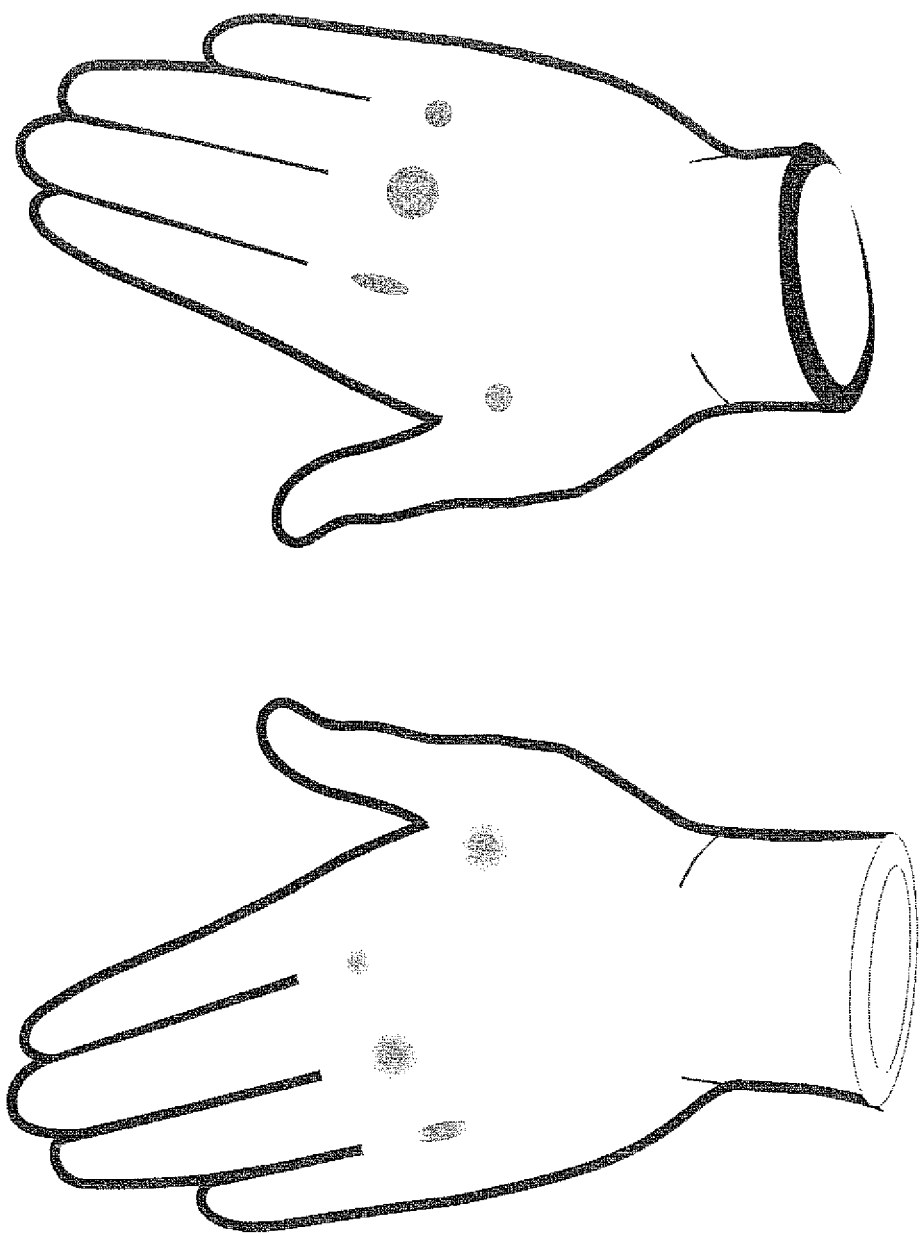
FIG. 1 schematically shows a glove adapted for use in the method of the invention.

The invention is guiding means that are adapted to serve as guides to accurately locate specific locations on the body to be stimulated in order to prevent, diagnose, and treat specific types of diseases and other conditions in humans and animals. The invention includes specially modified and personalized articles of clothing and an apparatus for supporting an organ of a human or animal body adapted for accurately positioning and orienting the organ with respect to each other a device for administering the stimulation or the healing process. The apparatus and embodiments of the articles of clothing are adapted as stands that support devices used to apply stimulation to the location. The applied stimulation can be any of the therapies which depend on the application of energy or force to specific locations on the body. No generic name is known to the inventor that includes all of the therapies and techniques to which the devices of the invention can usefully be applied; however these include e.g. traditional needle acupuncture, laser acupuncture, acupuncture using both needles and laser simultaneously in a single treatment session, and devices or methods for applying non-coherent light, pressure, heat, electricity. The treatments can be carried out by accredited practitioners in a clinical setting or by inexperienced persons including the patient her/himself at home. In order to illustrate the invention the description herein discusses the application of the guiding means of the invention to acupuncture therapy; however it is important to keep in mind that the guiding means can be applied to other bio-stimulation techniques and healing procedures including application of soft laser therapy.

One of the reasons that traditional acupuncture treatments can only be administered by registered practitioners is the long learning curve need to learn how to locate the acupoints on the human or animal body that will most effectively stimulate self-healing of a specific condition in a specific organ and, once the acupoint has been located to accurately insert the needle. Assuming that the approximate location of the acupoint is known, the success of the treatment depends on the accuracy of placement of the needle, the angle, and the pattern at which the needle is inserted, which in some cases is not perpendicular to the skin surface. Practitioners of laser acupuncture experience the same difficulties since most devices used in laser acupuncture produce an output beam having a small footprint on the skin (typically a round footprint with a diameter of approximately 1 mm and an area of approximately 0.8 $mm^2$).

To overcome the problems associated with the level of exactness required when using needles or small diameter laser beams and to make it possible for non-professionals, including the patient her/himself to administer the treatment following a protocol recommended by a licensed practitioner the inventor of the present invention has conceived of the idea of using a laser device that produces a beam of laser light having a large cross-sectional area; for example a long and narrow beam, which can be aligned with the meridian and centered approximately at the location of the acupoint. The device produces a fully coherent output beam (having an energy density that is uniform in magnitude over the entire rectangular, elliptical, or circular footprint, which in a non-limiting, illustrative embodiment can be approximately 100 mm². Using a laser device that produces an output beam having a large footprint on the skin that is powerful enough to stimulate the acupoint means that the center of the laser beam does not have to be located exactly over the acupoint.

As mentioned above, one of the reasons that acupuncture treatments are carried out only by licenced practitioners is the level of experience necessary to accurately locate the acupuncture point and to insert the needle or align the laser beam. The present invention overcomes these problems by providing the following aids at least one of which can be employed by the user to assist him/her to accurately locate and stimulate the required acupoints:

A stimulation source in the form of a hand held device that illuminates a rectangular, elliptical, or round area of the skin of the patient with light. An embodiment of the light emitting stimulation source is a laser device that emits infrared radiation and comprises a second light source that emits a visible light that overlaps or outlines the invisible beam emitted by the infrared laser diode;

Personalized articles of clothing, e.g. a glove (for acupoints on the hand), a sock (for acupoints on the foot), a cap or helmet (for acupoints on the head), a belt (for other areas of the body), that comprises holes directly over the acupoints corresponding to the points that should be stimulated for the specific condition.

An apparatus that is adapted to position and to support the stimulation means, e.g. laser device or needle, above the acupoint at the correct location and angle.

A video camera can be used to observe the relevant body part and produce images that, when used in conjunction with a processor and appropriate software and optionally with input from an experienced practitioner, can be displayed to the user to enable him/her to locate the desired acupoint and to insert the needle or aim the laser beam to that spot. In embodiments of the invention the user and the licensed acupuncturist, veterinarian, or doctor are at separate locations. Both possess devices, e.g. smartphones, tablets, or computers, comprising dedicated software and connected to a communication network, e.g. the internet or a cellular network, which allows them to share images taken by the video camera and other information and to communicate with each other. In these embodiments the practitioner can be actively involved in the home treatment session, for example by marking the location of the acupoint/s to be treated on the screen image of the patient.

FIG. 1 schematically shows a glove adapted for use in the method of the invention. The glove is provided in a number of sizes and in left and right hand versions to insure a correct fit to the hand of the patient.

Unpersonalized gloves can be produced in a number of models, each with pre-cut holes at the known location of the acupoints for treatment of one or more types of disease or conditions. Embodiments of the unpersonalized gloves will be made available with the size, and the name of the disease/s the holes represent printed on them.

The glove, or at least part of it, can be made from transparent material, to assist in locating the acupoint. Other items of clothing such as a sock or a belt to be fastened around different portions of the body can be adapted mutatis mutandis for use in the method of the invention in a manner similar to the glove shown in FIG. 1.

Alternatively, the attending physician, veterinarian, or accredited acupuncture practitioner that recommends and supervises the treatment can personalize the glove by creating holes at the location of the acupoints that are appropriate for the specific symptoms of his patient. In order to individualize the article of clothing such that the placement of the holes conforms to the exact anatomical structure and dimensions of the patient, embodiments of the articles of clothing are manufactured with at least a part of the article of clothing made of transparent material. In the first session with the practitioner, the patient puts on the article of clothing having the closest fit to her/his body and the practitioner locates the appropriate acupoint/s on the patient's body, marks the location/s on the article of clothing, and makes holes of the required size. The practitioner may use standard techniques to locate the acupoints and mark them on the skin before she/he puts on the article of clothing. The marks on the skin can then be seen through the transparent material and transferred to the article of clothing to mark the locations at which the holes should be created.

These holes allow the patient to apply the acupuncture treatment by him/herself, whether using an acupuncture needle, a prior art narrow beam laser device or the wide beam laser device described herein above or any other device used to stimulate acupoints. In addition to the use of conventional acupuncture needles the inventor envisages that an acupuncture needle supplied as an auto-injector similar to those used to inject insulin would be a very useful aid to many patients.

Embodiments of the articles of clothing comprise ridges around the holes or have a framework attached to them over the holes. The ridges or framework are adapted to help to hold the device used to apply the stimulation in a fixed position and orientation over the acupoint.

Figure 2:
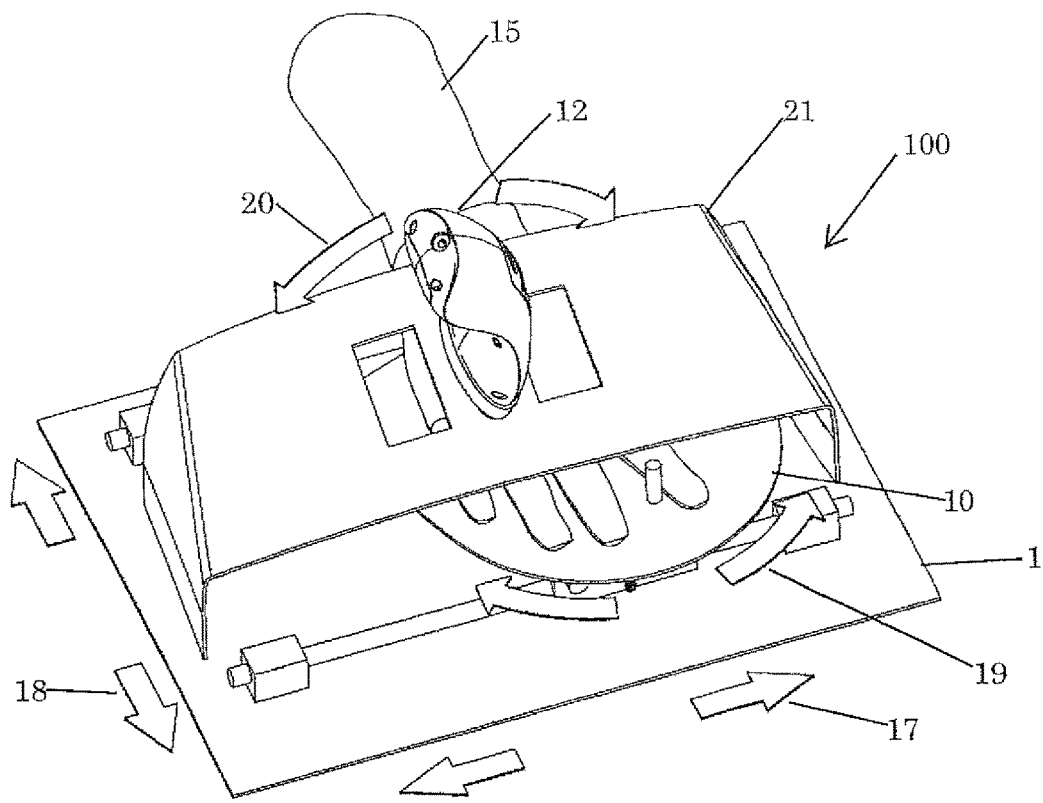
FIG. 2 to FIG. 4B schematically show an apparatus adapted to allow experienced and inexperienced persons to administer acupuncture treatment.
Figure 3:
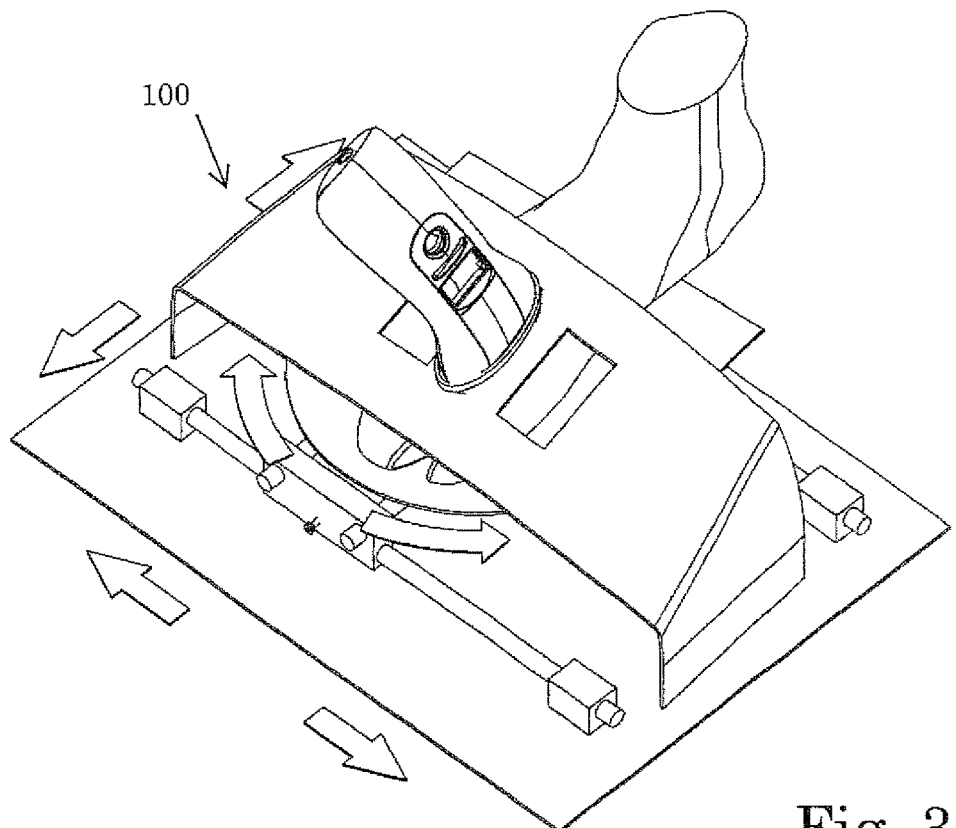

FIG. 2 to FIG. 4B schematically show an apparatus adapted to allow an inexperienced person to administer acupuncture treatment. The apparatus is designed to position the stimulation device at the correct location over the acupoint and at the correct angle and to support the device during the treatment period. FIG. 2 shows the apparatus adapted for use with a hand. FIG. 3 shows the apparatus adapted for use with a foot. The main features of apparatus 100 are identified in FIG. 2. Other components of apparatus 100 are described in more detail with respect to FIG. 4A and FIG. 4B.

The framework of apparatus 100 that supports all other components is comprised of a base plate 1 to which is rigidly attached a rigid bridge 21. Between the base plate 1 and bridge 21 is located a platform 10. Platform 10 is mounted in such a way that it has two linear degrees of freedom—back and forth and right and left motion in directions parallel to two perpendicular sides of base plate 1 (indicated by arrows 17 and arrows 18)—and one rotational degree of freedom—clockwise and counterclockwise (indicated by arrows 19) around an axis perpendicular to base plate 1 that passes through the center of platform 10. In the center of the bridge is at least one opening through which the laser device 12 is placed so that it can irradiate the surface of platform 10. A framework 13 which supports laser device 12 is attached to the bridge at the edge of the opening by means of a hinge adapted to allow laser device 12 to be tilted (indicated by arrows 20) relative to the surface of bridge 21. The tilt of the laser device gives the apparatus a fourth degree of freedom, which is important because some of the acupoints are located on the side of a bone and have to be stimulated at an angle to the perpendicular to achieve a positive result from the treatment. The organ 15 being treated is placed on the platform 10, which is moved until the location of the acupoint to be treated is under the center of the laser device 12. Platform 10 is now fixed in the correct position and at the correct orientation by locking its tilt angle and linear and rotational movements and the treatment can be started. In embodiments of the invention the locking mechanisms for the translational, rotational, and tilt motions comprise a series of marks that identifies the position at which each of the respective mechanisms is locked. After the initial location of the point at which the therapy should be applied is determined by the practitioner, the values of these marks are recorded and form a part of the treatment protocol for the patient, enabling the correct location for applying the therapy to be easily found in subsequent sessions.

In embodiments of the invention an article of clothing similar to that shown in FIG. 1 is used in conjunction with apparatus 100 in order to more easily locate the desired acupoint.

Figure 4A:
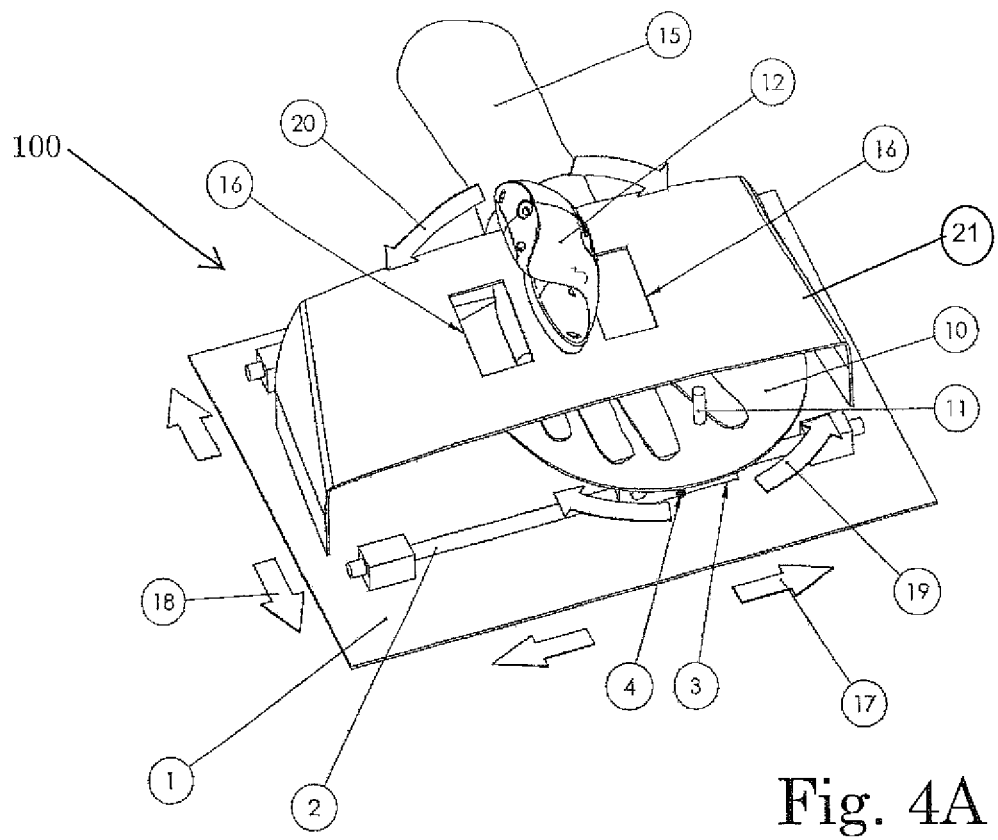
Figure 4B:
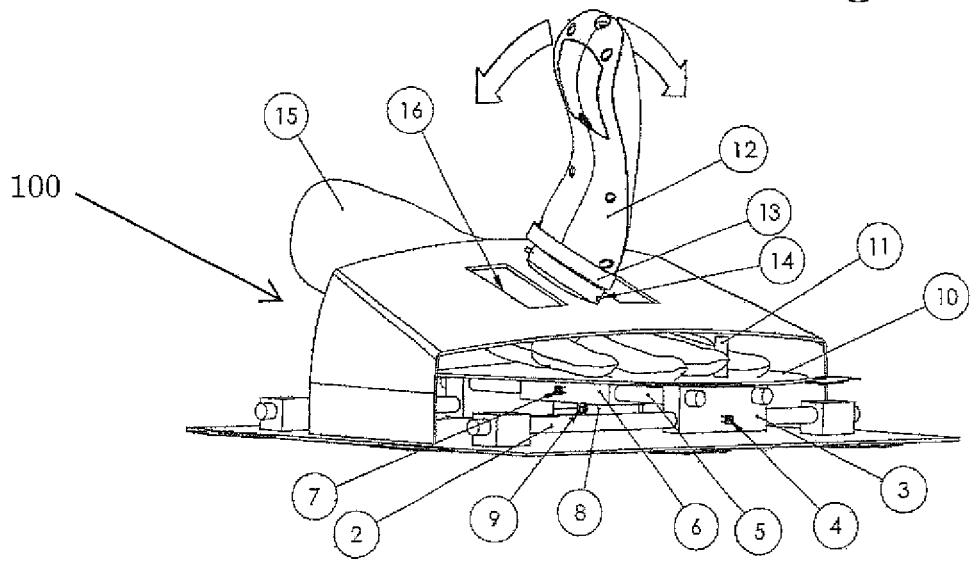

Referring to FIG. 4A and FIG. 4B other components of apparatus 100 are:
X-direction rail 2, two parallel rails 2 are attached on opposite sides of base plate 1;
X-direction carriage 3, one of which rides on each of rails 2;
X-direction carriage lock 4, which, when locked, prevents movement of carriage 3 along rail 2;
Y-direction rail 5, two parallel rails 5 are attached at their ends to the two carriages 3;
Y-direction carriage 6, one of which rides on both of rails 5;
Y-direction carriage lock 7, which, when locked, prevents movement of carriage 6 along rails 5;
Z-axis pivot 8, which is attached to carriage 6 and supports platform 10;
Z-axis lock 9, which, when locked, prevents rotation of platform 10;
Locating pins 11, used to position the organ 15 to be treated, e.g. hand, on platform 10 and to maintain that position during the alignment and treatment procedures;
Framework 13 of laser device 12;
Hinge 14 that connects framework 13 to bridge 21 of apparatus 100 (not shown in the figures is a lock to prevent tilt of laser device 12); and
Windows 16 or openings in the top of bridge 21 that allow observation of the treatment area on the organ 15 being treated.

In the figures the apparatus 100 is adapted for use with a wide beam laser device but apparatus 100 can be modified mutatis mutandis for use with any device that is used to apply acupuncture treatment, e.g. conventional acupuncture needles, other types of laser devices, non-laser light sources, and acupuncture needles supplied as auto-injectors. In addition, apparatus 100 can be adapted mutatis mutandis for placement and support of an acupuncture device over acupoints located at locations on the bodies of humans and animals besides hands and feet.

Because apparatus 100 supports the stimulation and healing device during treatment, it is especially useful in a clinical environment where the use of several of these apparatuses will allow a single practitioner to simultaneously treat several acupoints on the same patient, e.g. the corresponding point on the right and left hand, or to treat several patients simultaneously. The use of more than one apparatus will erase the advantage that the use of needles has over lasers in treatment protocols that require stimulation of several acupoints on the same patient to be treated at once.

During acupuncture treatment sessions using either needles or laser devices some human patients report feeling sensations, which are usually described as a very moderate uneasiness and slight pain in the affected organ, and are interpreted to mean that something "is happening" in the relevant organ. Having these sensations does not mean that the treatment will work better, but it is a good sign, which helps the patient to gain confidence in the treatment. In cases where good results are achieved, the patients feel the sensations with increasing lower intensity as the sessions progress and simultaneously the acupoints may become less sensitive. Observing this phenomenon has led the inventor to the conclusion that stimulating the acupoints one at a time in any of the ways described above and receiving feedback from the patient can be used for early diagnosis of disease in the organ associated with the specific acupoint. The diagnosis can then be confirmed or dismissed by other tests.

Because using the laser acupuncture in combination with either the modified article of clothing, e.g. glove, or apparatus of the invention is easy to do at home, it is recommended to individuals at high risk of contracting a specific type of disease, as determined by family history or their genetic makeup, to follow a protocol of laser radiation of the specific acupoint/s associated with that disease as a preventive treatment.

Although embodiments of the invention have been described by way of illustration, it will be understood that the invention may be carried out with many variations, modifications, and adaptations, without exceeding the scope of the claims.

The invention claimed is:

1. An apparatus adapted to support and to accurately position and orient an hand or foot of a human or an animal and a device adapted for administering acupuncture, bio-stimulation, and other therapies and healing procedures with respect to each other at a specific location on the hand or foot of the human or animal to prevent, diagnose, and treat specific types of diseases and other conditions in the human or animal, the apparatus comprising:
   a) a base plate configured to support all other components of the apparatus;
   b) a rigid bridge rigidly attached to the base plate;
   c) a platform configured to allow the hand or foot to be placed on it, the platform located above the base plate and below the bridge, the platform mounted to the base plate in such a way that it has two linear degrees of freedom that allow linear motion in directions parallel to two perpendicular sides of the base plate and one rotational degree of freedom around an axis perpendicular to the base plate that passes through the center of the platform;
   d) at least one window or opening in the top of the bridge configured to allow observation of the specific location on the hand or foot at which the treatment is being applied when the hand or foot is positioned on the platform;
   e) at least one opening in the top of the bridge configured to allow the device adapted for administering acupuncture, bio-stimulation, and other therapies and healing procedures to stimulate, through the opening, the specific location on the hand or foot of the human or animal that is placed on the platform; and
   f) a framework configured to support the device adapted for administering acupuncture, bio-stimulation, and other therapies and healing procedures, the framework attached to the top of the bridge at the edge of the opening through which the device adapted for administering acupuncture, bio-stimulation, and other therapies and healing procedures can apply treatment by a hinge configured to allow the device adapted for administering acupuncture, bio-stimulation, and other therapies and healing procedures to be tilted relative to the surface of the bridge.

2. The apparatus of claim 1 wherein the device that is adapted for administering acupuncture, bio-stimulation, and other therapies and healing procedures is one of: traditional acupuncture needles, acupuncture needles supplied as auto-injectors, a laser beam, a device for applying non-coherent light, a device for applying pressure, a device for applying heat, and a device for applying electricity or a combination of them.

3. The apparatus of claim 1, comprising locking mechanisms for the translational, rotational, and tilt motions.

4. The apparatus of claim 3, wherein the locking mechanisms comprise a series of marks that identifies the position at which each of the respective locking mechanisms is locked.

\* \* \* \* \*